(12) United States Patent
Johs

(10) Patent No.: US 6,268,917 B1
(45) Date of Patent: Jul. 31, 2001

(54) COMBINED POLYCHROMATIC ELECTROMAGNETIC BEAM SOURCE SYSTEM WITH APPLICATION TO ELLIPSOMETERS, SPECTROPHOTOMETERS AND POLARIMETERS

(75) Inventor: Blaine D. Johs, Lincoln, NE (US)

(73) Assignee: J.A. Woollam Co. Inc., Lincoln, NE (US)

( * ) Notice: Subject to any disclaimer, the term of this patent is extended or adjusted under 35 U.S.C. 154(b) by 0 days.

(21) Appl. No.: 09/479,091

(22) Filed: Jan. 7, 2000

Related U.S. Application Data

(63) Continuation-in-part of application No. 09/246,888, filed on Feb. 8, 1999, now Pat. No. 6,084,675, which is a continuation-in-part of application No. 08/912,211, filed on Aug. 15, 1997, now Pat. No. 5,872,630, which is a continuation-in-part of application No. 08/530,892, filed on Sep. 20, 1995, now Pat. No. 5,666,201, which is a continuation-in-part of application No. 08/947,430, filed on Sep. 18, 1992, now Pat. No. 5,373,359, which is a continuation-in-part of application No. 08/618,820, filed on Mar. 20, 1996, now Pat. No. 5,706,212.

(51) Int. Cl.$^7$ ............................................. G01J 4/00
(52) U.S. Cl. ....................... 356/369; 356/356; 250/225
(58) Field of Search ............................ 356/369, 364, 356/365, 366, 367, 368; 250/225

(56) References Cited

U.S. PATENT DOCUMENTS

| | | | |
|---|---|---|---|
| 3,947,688 | 3/1976 | Massey | 250/495 |
| 4,053,232 | 10/1977 | Dill et al. | 356/118 |
| 4,668,086 | 4/1987 | Redner | 356/33 |
| 4,982,206 | 1/1991 | Kessler et al. | 346/108 |
| 5,002,371 | 3/1991 | Wright | 350/394 |
| 5,113,279 | 5/1992 | Hanamoto et al. | 359/196 |
| 5,155,623 | 10/1992 | Miller et al. | 359/495 |
| 5,179,462 | 1/1993 | Kageyama | 359/204 |
| 5,296,958 | 3/1994 | Roddy et al. | 359/204 |
| 5,329,357 | 7/1994 | Bernoux et al. | 356/369 |
| 5,373,359 | 12/1994 | Woollam et al. | 356/328 |
| 5,416,588 | 4/1995 | Ducharme et al. | 356/369 |
| 5,504,582 | 4/1996 | Johs et al. | 356/369 |
| 5,521,706 | 5/1996 | Green et al. | 356/369 |
| 5,581,350 | 12/1996 | Chen et al. | 356/369 |
| 5,596,406 | 1/1997 | Rosencwaig et al. | 356/327 |
| 5,666,201 | 9/1997 | Johs et al. | 356/369 |
| 5,706,212 | 1/1998 | Thompson et al. | 364/525 |
| 5,805,285 | 9/1998 | Johs et al. | 356/369 |
| 5,872,630 | 2/1999 | Johs et al. | 356/369 |
| 5,877,859 | 3/1999 | Aspnes et al. | 356/364 |
| 5,917,594 | 6/1999 | Norton | 356/327 |

*Primary Examiner*—Frank G. Font
*Assistant Examiner*—Reginald A. Ratliff
(74) *Attorney, Agent, or Firm*—James D. Welch

(57) ABSTRACT

Disclosed is a source of polychromatic electromagnetic radiation which, utilizing a beam combiner system, combines beams of polychromatic electromagnetic radiation from a plurality of sources to provide a relatively broad and flattened intensity characteristic vs. wavelength output spectrum, and its application in material system investigation systems, such as ellipsometers, spectrophotometers and polarimeters which comprise a polychromatic source of electromagnetic radiation.

18 Claims, 6 Drawing Sheets

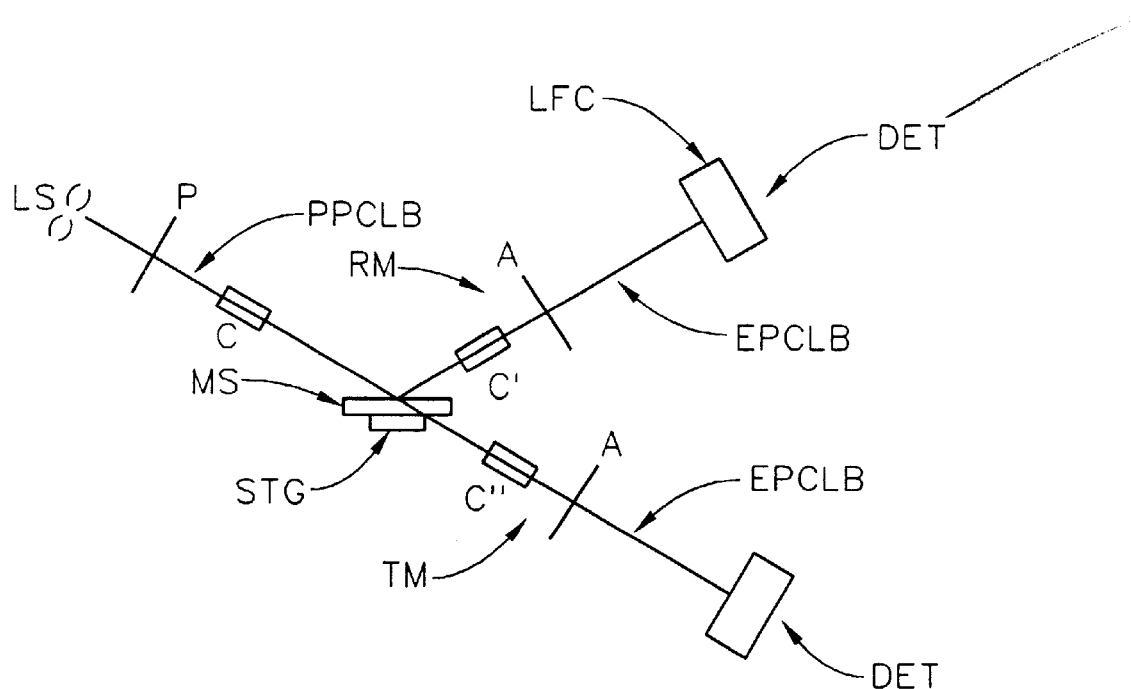
FIG. 1
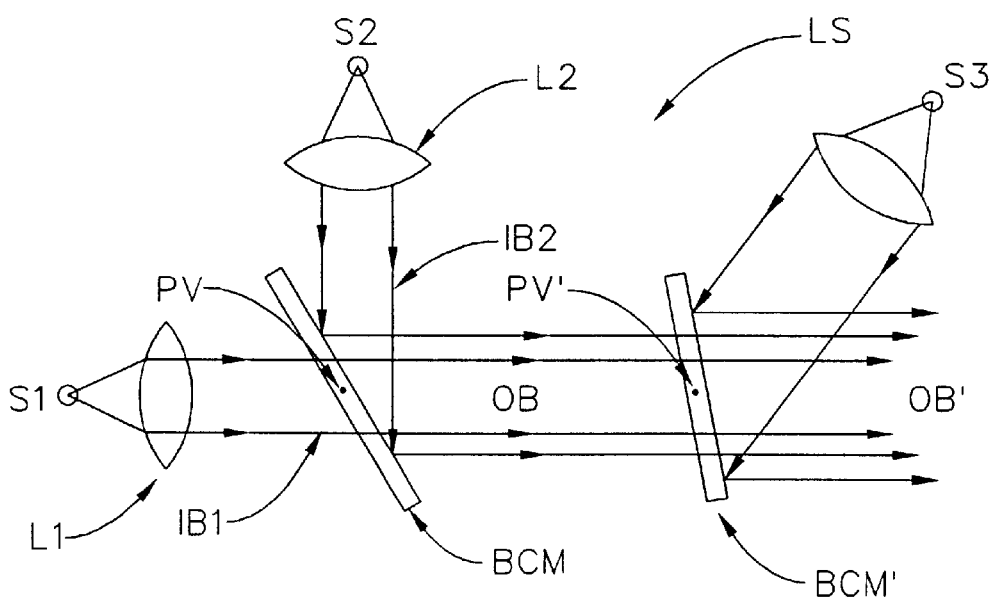
FIG. $2a_1$

FIG. $2a_2$

COMBINED POLYCHROMATIC ELECTROMAGNETIC BEAM SOURCE SYSTEM WITH APPLICATION TO ELLIPSOMETERS, SPECTROPHOTOMETERS AND POLARIMETERS

This Application is a Continuation-In-Part of co-pending application Ser. No. 09/246,888 filed Feb. 08, 1999 now U.S. Pat. No. 6,084,675 which was a CIP from application Ser. No. 08/912,211 filed Aug. 15, 1997, (now Pat. No. 5,872,630), which was a CIP from application Ser. No. 08/530,892 filed Sep. 20, 1995, (now Pat. No. 5,666,201) which was a CIP from application Ser. No. 08/947,430 filed Sep. 18, 1992, (now Pat. No. 5,373,359); and is a CIP of application Ser. No. 08/618,820 filed Mar. 20, 1996, (now Pat. No. 5,706,212).

TECHNICAL FIELD

The present invention relates to material system investigation systems, such as ellipsometers, spectrophotometers and polarimeters which comprise a polychromatic source of electromagnetic radiation, and more particularly to a source of polychromatic electromagnetic radiation which, via beam combiner means, combines beams of polychromatic electromagnetic radiation from a plurality of sources, to provide a relatively broad and flat intensity characteristic vs. wavelength output spectrum.

BACKGROUND

The use of material system investigation systems, (such as ellipsometer systems), to investigate material systems, (such as substrates with thin films present thereupon), is well known.

As insight, an ellipsometer system is, for instance, comprised of a source of electromagnetic radiation, a polarization state setting system, a means for supporting a material system, and a polarization state detecting system comprised of an analyzer and a detector system. In addition compensators(s) can be present between the source of electromagnetic radiation and the detector system, often as part of a polarization state setting system.

A number of types of ellipsometer systems exist, such as those which include rotating elements and those which include modulation elements. Those including rotating elements include Rotating Polarizer (RP), Rotating Analyzer (RA) and Rotating Compensator (RC). In particular it is noted that Rotating Compensator Ellipsometer Systems do not demonstrate "dead-spots" where obtaining data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "dead spots" at DELTA's near 0.0 or 180 Degrees and Modulation Element Ellipsometers also have "Dead Spots" at PSI near 45 Degrees. Another benefit provided by fixed Polarizer (P) and Analyzer (A) positions in rotating compensator ellipsometer systems is that polarization state sensitivity to input and output optics during data acquisition is essentially non-existent. This enables relatively easy use of optic fibers, mirrors, lenses etc. for input/output.

Continuing, it is generally known that a source of electromagnetic radiation can provide a monochromatic, (eg. a laser system), or a polychromatic output. In spectroscopic ellipsometer systems, a polychromatic source of electromagnetic radiation is utilized to enable obtaining data at numerous wavelengths simultaneously. Typically available sources of polychromatic electromagnetic radiation, however, do not provide similar intensity output at all wavelengths, let alone a relatively broad and flat magnitude vs. wavelength spectra. As a result, data can not be obtained at all wavelengths over a wide range thereof.

A need is thus identified for a source of polychromatic electromagnetic radiation which can combine wavelength spectra from multiple polychromatic electromagnetic radiation sources, to provide a relatively broad and flattened intensity vs. wavelength spectra in material system investigation systems.

With the present invention in mind, a Search of Patents for sources of broad band polychromatic electromagnetic radiation was conducted, and said Search has identified Patents which describe systems which combine wavelengths from a plurality of laser sources to provide a single output beam of electromagnetic radiation that contains wavelengths provided by all said sources. In particular said Search revealed numerous Patents wherein a beam of electromagnetic radiation comprising wavelengths present in a plurality of laser sources is achieved by use of electromagnetic beam combining dichroic mirrors as an enabling means. U.S. Pat. No. 5,179,462 to Kageyama et al. for instance, provides a sequence of three such electromagnetic beam combining dichroic mirrors in an arrangement which produces an output beam of electromagnetic radiation that contains wavelengths from each of four sources of electromagnetic radiation. Each electromagnetic beam combining dichroic mirror is arranged so as to transmit a first input beam of electromagnetic radiation, comprising at least a first wavelength content, therethrough so that it exits a second side of said electromagnetic beam combining dichroic mirror, and to reflect a second beam of electromagnetic radiation, comprising an additional wavelength content, from said second side of said electromagnetic beam combining dichroic mirror in a manner that a single output beam of electromagnetic radiation is formed which contains the wavelength content of both sources of electromagnetic radiation. The sources of electromagnetic radiation are described as lasers in said 462 Patent. Another Pat. No. 5,296,958 to Roddy et al., describes a similar system which utilizes Thompson Prisms to similarly combine electromagnetic beams for laser source. Pat. Nos. 4,982,206 and 5,113,279 to Kessler et al. and Hanamoto et al. respectively, describe similar electromagnetic electromagnetic beam combination systems in laser printer and laser beam scanning systems respectively. Another Pat., No. 3,947,688 to Massey, describes a method of generating tuneable coherent ultraviolet light, comprising use of an electromagnetic electromagnetic beam combining system. A Patent to Miller et al., No. 5,155,623, describes a system for combining information beams in which a mirror comprising alternating regions of transparent and reflecting regions is utilized to combine transmitted and reflected beams of electromagnetic radiation into a single output beam. A Patent to Wright, No. 5,002,371 is also mentioned as describing a beam splitter system which operates to separate "P" and "S" orthogonal components in a beam of polarized electromagnetic radiation.

Patents assigned to the J. A. Woollam Co. Inc., which describe material system investigation systems such as ellipsometers, spectrophotometers and polarimeters include No. 5,373,359 to Woollam et al., Nos. 5,872,630 and 5,666,201 and 5,805,285 to Johs et al., Nos. 5,521,706 and 5,504,582 to Green et al and Johs et al. respectively, No. 5,706,212 to Thompson et al. In addition a modulation element ellipsometer system is described in Patent No. 5,416,588 to Ducharme et al. Said just recited Patents are hereby included herein by reference.

Said 359 Patent describes a Rotating Analyzer ellipsometer system, and the 201 Patent comprises a detector arrangement in which multiple orders of a dispersed beam of electromagnetic radiation are intercepted by multiple detector systems. Said 212 Patent describes use of an Achromatic Rotating Compensator and application of Mathematical Regression in a Calibration procedure which evaluates calibration parameters in both rotating and stationary components. Said 630 Patent was Continued-in-Part therefrom and describes a particularly relevant ellipsometer system in which the present invention can be beneficially applied. In particular said 630 Patent describes a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements.

Another, and recent, Patent to Aspnes, is No. 5,877,859. This Patent describes a Broadband Spectroscopic Rotating Compensator Ellipsometer System wherein the Utility is derived from selecting a Wavelength Range and Compensator so that at least one wavelength in said wavelength Range has a retardation imposed of between 135 and 225 Degrees, and another wavelength in the wavelength Range has a retardation imposed which is outside that retardation Range. The entire Utility of the Therma-wave Patent derives from that condition being met so that coefficients of two-omega and four-omega terms at various wavelengths provide information, even when other such coefficients do not.

A Pat., No. 4,053,232 to Dill et al. describes a Rotating-Compensator Ellipsometer System, which operates utilizes monochromatic light. Two Patents which identify systems which utilize Polychromatic light in investigation of material systems are described in Pat. Nos. 5,596,406 and 4,668,086, to Rosencwaig et al. and Redner, respectively, were also identified. A Patent to Bernoux et al., No. 5,329,357 is identified as it describes the use of optical fibers as input and output means in an ellipsometer system. A Patent to Chen et al., No. 5,581,350 is identified as it describes the application of regression in calibration of ellipsometer systems. An article by Johs, titled "Regression Calibration Method For Rotating Element Ellipsometers", which appeared in Thin Film Solids, Vol. 234 in 1993 is also identified as it predates the Chen et al. Patent and describes an essentially similar approach to ellipsometer calibration. An article by Jellison Jr. titled "Data Analysis for Spectroscopic Ellipsometry", Thin Film Solids, 234, (1993) is identified as it describes a method of determining the accuracy with which certain data points can be measured, which information allows adding a weighting factor to a curve fitting regression procedure as applied to a multiplicity of data points, said weighting factor serving to emphasize the effect of more accurate and precise data. A book by Azzam and Bashara titled "Ellipsometry and Polarized light"North-Holland, 1977 is disclosed and incorporated herein by reference for general theory. An article by Collins titled "Automated Rotating Element Ellipsometers: Calibration, Operation, and Real-Time Applications", Rev. Sci. Instrum. 61(8), August 1990 is identified as it provides insight into rotating element ellipsometers. Finally, a presentation at a Materials Research Society Symposium between Apr.6–7, 1999, in San Francisco, Calif., by Zapien, Collins and Messier, titled "Extension Of Multichannel Spectroscopic Ellipsometry Into The Ultraviolet For Real Time Characterization Of The Growth Of Wide Bandgap Materials From 1.5 to 6.5 eV", is included because a source of electromagnetic radiation which combines electromagnetic radiation from two souces is described.

No Patent or Article, however, was discovered which alone or in combination describes the use of electromagnetic beam combining systems to form a relatively broad and flattened beam of electromagnetic radiation which contains a combined spectrum of wavelengths originating from separate polychromatic sources of electromagnetic radiation. This is particularly true in the context of application in material system investigation systems, such as ellipsometers, spectrophotometers and polarimeters which contain a polychromatic source of electromagnetic radiation.

DISCLOSURE OF THE INVENTION

The present invention is primarily a source of polychromatic electromagnetic radiation which provides as output a relatively broad and flattened intensity vs. wavelength spectrum, said relatively broad and flattened intensity vs. wavelength spectrum substantially being the resultant combination of a plurality of input polychromatic wavelength spectra which originate from a plurality of sources, each of said plurality of sources providing a polychromatic, but relatively limited intensity vs. wavelength spectrum range. The present invention is particularly well suited for application in material system investigation systems such as ellipsometer, spectrophotometer and polarimeter systems which contain sources of electromagnetic radiation.

The present invention is further found in a combination of a source of polychromatic electromagnetic radiation which provides as output a relatively broad and flattened intensity vs. wavelength spectrum, with material system investigation systems.

For example, a present invention application can be recited as a material system investigation system, such as an ellipsometer, or polarimeter including a source of a polychromatic beam of electromagnetic radiation, said material system investigation system comprising:

a. a source of a beam of polychromatic electromagnetic radiation;

b. a polarization state setting system;

c. a means for supporting a material system; and d. a polarization state detection system. In use a beam of polychromatic electromagnetic radiation is caused to be provided by the source of a beam of polychromatic electromagnetic radiation, pass through said polarization state setting system, interact with a material system on said means for supporting a material system, and enter said polarization state detection system. Further, the material system investigation system polarization state setting system is typically comprised of a polarizer, optionally combined with a compensator, and the polarization state detection system is typically comprised of an analyzer and a multi-element containing detector system for simultaneously intercepting a plurality of wavelengths.

A preferred application of the present invention can be recited as a spectroscopic rotating compensator material system investigation system comprising a source of a beam of polychromatic electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned:

before said stage for supporting a material system; or after said stage for supporting a material system; or both before and after said stage for supporting a material system. When said spectroscopic rotating compensator material system investigation system is used to investigate a material system present on said stage for supporting a material system, the analyzer and polarizer are maintained essentially fixed in position and at least one of said at least one compensator(s) is caused to continuously rotate while a beam of polychromatic electromagnetic radiation produced by said source of a beam of polychromatic electromagnetic radiation is caused to pass through said polarizer and said compensators. The beam of polychromatic electromagnetic radiation is also caused to interact with said material system, pass through said analyzer and interact with said dispersive optics such that a multiplicity of essentially single wavelengths are caused to simultaneously enter a corresponding multiplicity of detector elements in said at least one detector system. The spectroscopic rotating compensator material system investigation system can utilize compensator(s) which is/are achromatic, or non-achromatic in that retardation effected thereby between orthogonal components of a beam of electromagnetic radiation at one wavelength is different than that provided thereby at least one other wavelength.

Another recitation of the present invention application is a spectroscopic material system investigation system comprising a source of a beam of polychromatic electromagnetic radiation, a polarizer, a stage for supporting a material system, an analyzer, a dispersive optics and at least one detector system which contains a multiplicity of detector elements, said spectroscopic material system investigation system optionally comprising one or more compensator(s) positioned:

before said stage for supporting a material system;or after said stage for supporting a material system; or before and after said stage for supporting a material system; When the spectroscopic material system investigation system is used to investigate a material system present on said stage for supporting a material system, one or both of the polarizer and the analyzer is caused to continuously rotate while a beam of polychromatic electromagnetic radiation produced by the source of a beam of polychromatic electromagnetic radiation is caused to pass through said polarizer and any present compensators(s) said polychromatic beam of electromagnetic radiation being also caused to interact with said material system and pass through said analyzer.

Yet another recitation of a present invention application is a spectroscopic material system investigation system comprising a source of a beam of polychromatic electromagnetic radiation, a polarizer, a stage for supporting a material system, an analyzer, a dispersive optics, at least one detector system which contains a multiplicity of detector elements, and at least one modulation element positioned:

before said stage for supporting a material system; or after said stage for supporting a material system; or before and after said stage for supporting a material system; When said spectroscopic material system investigation system is used to investigate a material system present on said stage for supporting a material system, at least one modulation element is caused to modulate a beam of polychromatic electromagnetic radiation produced by said source of a beam of polychromatic electromagnetic radiation and caused to pass through said polarizer, said polychromatic beam of electromagnetic radiation being also caused to interact with said material system and pass through said analyzer.

Another recitation yet of an application of a present invention is a spectroscopic material system investigation system adapted to sense characteristics of a material system comprising;

a source of a beam of polychromatic electromagnetic radiation;

a polarization state generator;

an analyzer; and a diffraction grating and a colliminator. The diffraction grating and colliminator are positioned so that electromagnetic radiation passing through the analyzer, without further focusing after interacting with the material system, transmits into said detector, wherein the diffraction grating reflects electromagnetic radiation into the detector at a predetermined angle with respect to a normal to the diffraction grating with a precision of at least plus or minus one-half degree.

Most importantly however, is that the present invention source of a beam of polychromatic electromagnetic radiation applied in any of the above recited material system investigation systems, comprises a system for providing an output beam of electromagnetic radiation which has a relatively broad and flattened intensity vs. wavelength characteristic over a wavelength spectrum, and provides an output beam of electromagnetic radiation which is substantially a composite of a plurality of input beams of electromagnetic radiation which individually do not provide as relatively broad and flat an intensity vs. wavelength characteristic over said wavelength spectrum, as does said output beam of electromagnetic radiation. In any embodiment thereof, the present invention then comprises at least a first and a second source of polychromatic electromagnetic radiation, and at least one electromagnetic beam combining means. (Note that a functionally acceptable, non-limiting, electromagnetic beam combining means is known in the art as a "dichroic mirror", however, non-coated thin glass or fused silica plates presenting with two essentially parallel surfaces work well and are preferred in the present invention). Said at least one electromagnetic beam combining means is positioned with respect to said first and second sources of polychromatic electromagnetic radiation such that a beam of electromagnetic radiation from said first source of electromagnetic radiation passes through said at least one electromagnetic beam combining means, and such that a beam of electromagnetic radiation from said second source of electromagnetic radiation reflects from said at least one electromagnetic beam combining means and is comingled along a common locus with said beam of electromagnetic radiation from said first source of electromagnetic radiation which passes through said at least one electromagnetic beam combining means. The comingled resultant beam of electromagnetic radiation is an output beam of polychromatic electromagnetic radiation which has a relatively broad and flattened intensity vs. wavelength over a wavelength spectrum, and comprises said composite of a plurality of input beams of polychromatic electromagnetic radiation which individually do not provide such a relatively broad and flattened intensity vs. wavelength over said wavelength spectrum characteristic.

A present invention system for providing an output beam of polychromatic electromagnetic radiation which has a relatively broad and flattened intensity vs. wavelength characteristic over a wavelength spectrum, said output beam of polychromatic electromagnetic radiation substantially being a comingled composite of a plurality of input beams of polychromatic electromagnetic radiation which individually do not provide as relatively broad and flattened an intensity vs. wavelength characteristic over said wavelength spectrum as does said output comingled composite beam of polychromatic electromagnetic radiation, then comprises:

a. at least a first and a second source of polychromatic electromagnetic radiation; and b. at least a first electromagnetic beam combining means. Again, the at least a first electromagnetic beam combining means is positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means. The resultant beam of polychromatic electromagnetic radiation is substantially the output beam of polychromatic electromagnetic radiation which has a relatively broad and flattened intensity vs. wavelength over a wavelength spectrum and comprises the comingled composite of a plurality of input beams of polychromatic electromagnetic radiation which individually do not provide such a relatively broad and flattened intensity vs. wavelength over a wavelength spectrum characteristic. The present invention system for providing an output beam of polychromatic electromagnetic radiation which has a relatively broad and flattened intensity vs. wavelength characteristic over a wavelength spectrum optionally further comprises:

a. a third source of polychromatic electromagnetic radiation; and b. a second electromagnetic beam combining means. When present, the second electromagnetic beam combining means is positioned with respect to said comingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means. The second electromagnetic beam combining means is also positioned with respect to said third source of polychromatic electromagnetic radiation, but such that a beam of electromagnetic radiation from said third source of polychromatic electromagnetic radiation reflects from said second electromagnetic beam combining means such that a second resultant beam of polychromatic electromagnetic radiation is produced which is substantially an output beam of polychromatic electromagnetic radiation which has a relatively even more broadened and flattened intensity vs. wavelength over a wavelength spectrum, comprising a comingled composite of a plurality of input beams of polychromatic electromagnetic radiation from said first, second and third sources, which first, second and third sources individually do not provide such a relatively even more broadened and flattened intensity vs. wavelength over a wavelength spectrum characteristic.

Further, at least one of said first and second, (when present), electromagnetic beam combining means can be pivotally mounted in said system for providing an output beam of polychromatic electromagnetic radiation which has a relatively broad and flattened intensity vs. wavelength characteristic over a wavelength spectrum to allow rotation thereof, said rotation serving to co-mingle and direct transmitted and reflected beams of electromagnetic radiation along a common locus. Additionally, where the sources of electromagnetic radiation can be moved, the pivoting allows adjusting the angle at which a beam of polychromatic electromagnetic radiation from said second source of polychromatic electromagnetic radiation reflects from said at least one electromagnetic beam combining means. This allows control of the relative amounts of transmission and reflection effected by an electromagnetic beam combining means.

Generally, in any of the foregoing embodiments, at least one electromagnetic beam combining means present therein can be pivotally mounted to allow two degrees of rotational freedom. This allows adjustment to effect co-mingled directing of transmitted and reflected beams of electromagnetic radiation along a common locus. And again, where a source of electromagnetic radiation is movable, the angle at which a beam of polychromatic electromagnetic radiation therefrom reflects from said electromagnetic beam combining means can be controlled by pivot adjustment, to control the amount of transmitted and reflected electromagnetic radiation in the resulting co-mingled electromagnetic beam.

Additionally, in any embodiment of the present invention, it is noted that the resulting output beam of polychromatic electromagnetic radiation which has a relatively broad and flattened intensity vs. wavelength over a wavelength spectrum can be caused to interact with a dispersive optics, said dispersive optics serving to form a plurality of essentially spatially offset orders (+ORD2) (+ORD1) (−ORD1) (−ORD2) when said beam of polychromatic electromagnetic radiation is caused to impinge thereupon, each said produced order (+ORD2) (+ORD1) (−ORD1) (−ORD2) comprising an essentially continuous spectrum of spatially separated electromagnetic beams of essentially single wavelengths, many of said essentially single wavelengths being present in two or more produced orders (+ORD2) (+ORD1) (−ORD1) (−ORD2). In use first and second multiplicities of essentially single wavelength beams of electromagnetic radiation from first and second produced orders can be simultaneously intercepted by, respectively, first and second detector systems, thereby enabling the simultaneous accessing of a first multiplicity of essentially single wavelengths by said first detector system and a second multiplicity of essentially single wavelengths by said second detector system. Each of the first and second multiplicities of essentially single wavelengths, it should be appreciated, includes specific first and second essentially single wavelength beams of electromagnetic radiation, and said specific first and second essentially single wavelength beams of electromagnetic radiation can be simultaneously intercept by specific detector elements in said first and second detector systems respectively, even where electromagnetic beams of said specific first and second essentially single wavelengths are spatially situated to close to one another in a single produced order for separate photo detector array detector elements in a single detector system which intercepts said single order.

Further, in any of the embodiments of the spectroscopic material system investigation systems where the polarizer remains fixed in position during data acquisition, (eg. in a rotating compensator system), it is prefereable that a source of electromagnetic radiation, and/or a present Polarizer or Polarization State Generator be positioned or configured so that predominately the "S" polarized electromagnetic radiation component, (as referenced to said beam combining system), is passed on to the material system being investigated. The reason for this is that the "S" polarization component split between transmitted and reflected components over a typical range of wavelengths and tilts of the electromagnetic beam combiner, compared to that for the "P" components, is far less in the electromagnetic beam combiners utilized in this invention. This is better described with reference to FIGS. 8a–8c in the Detailed Description Section of this Specification, but generally is explained by stating that a goal of the present invention is to provide as close to a constant intensity output electromagnetic beam as possible, as a function of wavelength and angle of incidence to an investigated material system. Where an "S" component, (referenced to a beam combining system), is utilized, it is to be appreciated that the difference in intensity of transmitted and reflected beams of electromagnetic radiation output from the present invention beam combining system, is minimized, as compared to variation which occurs in "P" components. Stated otherwise, "p" component, (referenced to a present invention electromagnetic beam combiner system), intensity in a transmitted electromagnetic beam is typically offset far more from "P" component intensity in reflection, (again referenced to a present invention electromagnetic beam combiner system), than is the case where "S" components are utilized. Again, FIGS. 8a–8c make this clear.

Finally, in any embodiment of a material system investigation system, fiber optics can be utilized to carry electromagnetic radiation from a source thereof, or to carry electromagnetic radiation to a detector system.

The present invention will be better understood by reference to the Detailed Description Section of this Disclosure, in conjunction with the Drawings.

SUMMARY OF THE INVENTION

It is therefore a primary objective and/or purpose of the present invention to teach a system for providing an output beam of polychromatic electromagnetic radiation which has a relatively broad and flattened intensity vs. wavelength characteristic over a wavelength spectrum, said output beam of polychromatic electromagnetic radiation substantially being a comingled composite of a plurality of input beams of polychromatic electromagnetic radiation which individually do not provide as relatively broad and flattened an intensity vs. wavelength characteristic over said wavelength spectrum, as does said output comingled composite beam of polychromatic electromagnetic radiation.

It is another objective and/or purpose of the present invention to teach that said system for providing an output beam of polychromatic electromagnetic radiation which has a relatively broad and flattened intensity vs. wavelength characteristic over a wavelength spectrum, can be beneficially combined with material system investigation systems.

It is yet another objective and/or purpose of the present invention to teach that where transmitted and reflected polychromatic beams of electromagnetic radiation are combined in a present invention beam combining system, and where a material system investigation system which operates with a fixed polarizer or polarization state generator is utilized, it is preferred practice to orient the electromagnetic beam combining system and/or fixed polarizer or polarization state generator such that the "S" component, (referenced to the electromagnetic beam combining system) is passed to a material system under investigation.

Other objectives and/or purposes of the present invention will be understood upon reference to the Specification.

BRIEF DESCRIPTION OF THE DRAWINGS

FIG. 1 demonstrates a Material System Investigation System, (eg. an Ellipsometer System), with provision to investigate a Material System (MS) in either a Reflection Mode (RM) or a Transmission Mode (TM).

FIG. 2a1 shows a present invention system for providing an output beam (OB) or (OB') of polychromatic electromagnetic radiation which has a relatively broad and flattened intensity vs. wave length characteristic over a wavelength spectrum.

FIG. 2a2 shows a present invention system for providing an output beam (OB) of polychromatic electromagnetic radiation which has a relatively broad and flattened intensity vs. wavelength characteristic over a wavelength spectrum, as in FIG. 2a1, but with the Beam Combining Means (BCM) rotated to change the angle at which the electromagnetic beam from (S2) reflects therefrom.

DETAILED DESCRIPTION

Figure 2B:
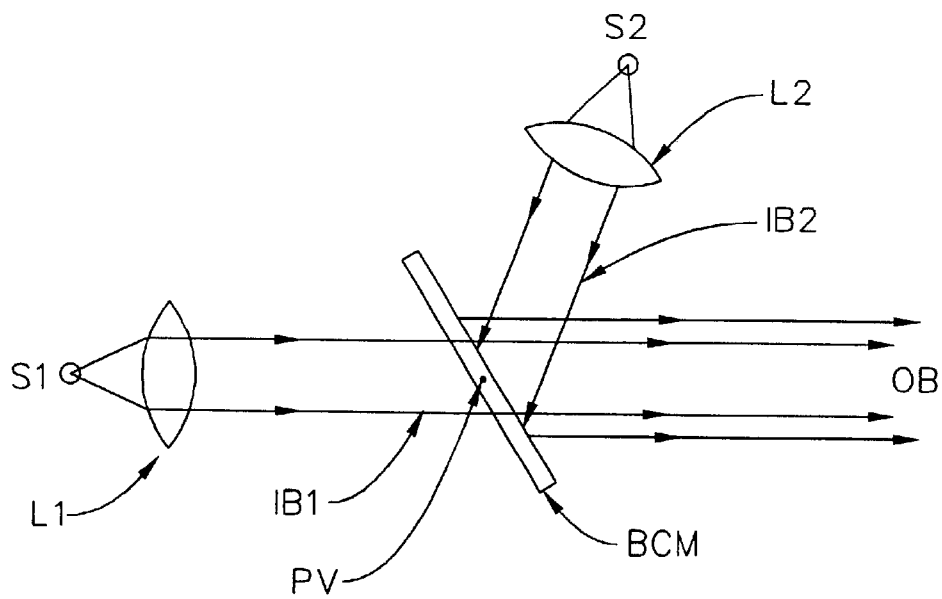
FIG. 2b demonstrates a spectrum of a polychromatic electromagnetic radiation (IBI) from said first source (S1) of polychromatic electromagnetic radiation which passes through said at least one electromagnetic beam combining means (BCM).
Figure 2B:
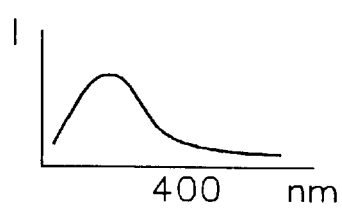

Referring now to FIG. 1, there is generally demonstrated a Material System Investigation System, (eg. an Ellipsometer System), with provision to investigate a Material System (MS) in either a Reflection Mode (RM) or a Transmission Mode (TM). It is to be noted that said Material System investigation System is generally comprised of a Source (LS) of a Polychromatic Beam of Electromagnetic Radiation, (see (OB) in FIG. 2), a Polarizer (P), a Material System supporting Stage (STG), an Analyzer (A) and a Detector Elements (DE's) containing Photo Array Detector System (DET). Also note, however, that FIG. 1 shows Reflection Mode System Compensator(s) (C) and (C') and Transmission Mode System Compensators (C) and (C") as demonstratively present. It is to be understood that a Compensator can be placed ahead of, and/or after a Material System (MS) supporting Stage (STC) in either a Reflection Mode or Transmission Mode System. That is only Compensator (C) or (C') or both Compensators (C) and (C') can be present in a Reflection Mode System (RM), and only Compensator (C) or (C") or both Compensators (C) and (C") can be simultaneously present in the Transmission Mode System (TM).

Now, the configuration in FIG. 1 could be operated as a Rotating Polarizer or Rotating Analyzer System, or as a Rotating Compensator Material System Investigation System. In the later, during Data Acquisition, the Polarizer (P) and Analyzer (A) are fixed while a Material System (MS) is placed upon the Material System supporting Stage (STG), and at least one present Compensator ((C), and/or (C') or (C) and/or (C")), is caused to Rotate. In a Rotating Polarizer or Rotating Analyzer the rotating element causes a continuous varying of the intensities of orthogonal components in a polarized beam of electromagnetic radiation, and a Rotating Compensator causes continuous variation of Retardence between Orthogonal Components in a Polarized Beam of Electromagnetic Radiation exiting said Compensator which is caused to rotate. Where two (2) Compensators are present, one before (C) and one after ((C') or (C")) a Material System placed upon said Material System (MS) supporting Stage (STG), only one, or both said Compensator(s) can be caused to Rotate in use. If both Compensators are present and caused to rotate, both can be rotated at the same rotation speed, or different rotation speeds can be utilized. It is further noted that fixing the Polarizer (P) and Analyzer (A) in use provides another benefit in that polarization state sensitivity to input and output optics during data acquisition is essentially non-existent. This allows convenient use of Optic Fibers, Mirrors, Lenses etc. for input/output.

Turning now to FIG. 2a1, it is shown that the present invention system for providing an output beam (OB) of polychromatic electromagnetic radiation which has a relatively broad and flattened intensity vs. wavelength characteristic over a wavelength spectrum (generally identified as (LS)), said output beam (OB) of polychromatic electromagnetic radiation substantially being a comingled composite of a plurality of input beams, ((IB1) and (IB2)), of polychromatic electromagnetic radiation which individually do not provide as relatively broad and flattened an intensity vs. wavelength characteristic over said wavelength spectrum, as does said output comingled composite beam of polychromatic electromagnetic radiation, comprises:

a. at least a first (S1) and a second (S2) source of polychromatic electromagnetic radiation, ((IB1) and (IB2) respectively); and b. at least one electromagnetic beam combining (BCM) means. The at least one electromagnetic beam combining means (BCM) is positioned with respect to said first (S1) and second (S2) sources of polychromatic electromagnetic radiation, ((IB1) and (IB2) respectively), such that a beam of polychromatic electromagnetic radiation (IB1) from said first (S1) source of polychromatic electromagnetic radiation passes through said at least one electromagnetic beam combining means (BCM), and such that a beam of polychromatic electromagnetic radiation (IB2) from said second (S2) source of polychromatic electromagnetic radiation reflects from said at least one electromagnetic beam combining means (BCM) and is comingled with said beam of polychromatic electromagnetic radiation (IB1) from said first source (S1) of polychromatic electromagnetic radiation which passes through said at least one electromagnetic beam combining means (BCM) along a common locus. The resultant beam of polychromatic electromagnetic radiation (OB) is substantially said output beam of polychromatic electromagnetic radiation which has a relatively broad and flattened intensity vs. wavelength over a wavelength spectrum, and comprises said comingled composite of a plurality of input beams of polychromatic electromagnetic radiation which individually do not provide such a relatively broad and flattened intensity vs. wavelength over a wavelength spectrum characteristic. Also shown in FIG. 2a1 are collimating lenses (L1) and (L2) to provide collimated electromagnetic radiation to the electromagnetic beam combining means (BCM), from first (S1) and a second (S2) source of polychromatic electromagnetic radiation, ((IB1) and (IB2) respectively).

Further shown in FIG. 2a1 is an optional third source of polychromatic electromagnetic radiation (S3) and a second electromagnetic beam combining means (BCM'). Said second electromagnetic beam combining means (BCM') is positioned with respect to said comingled beam of polychromatic electromagnetic radiation (OB), (which has a relatively broad and flattened intensity vs. wavelength over a wavelength spectrum, comprising wavelengths from sources (S1) and (S2), which exits said at least a first electromagnetic beam combining means (BCM)) such that said comingled beam of polychromatic electromagnetic radiation (OB) passes through said second electromagnetic beam combining means (BCM). Said second electromagnetic beam combining means (BCM) is further positioned with respect to said third source of polychromatic electromagnetic radiation (S3) such that a beam of electromagnetic radiation from said third source of polychromatic electromagnetic radiation (S3) reflects from said second electromagnetic beam combining means (BCM) to form a second resultant beam of polychromatic electromagnetic radiation (OB') which is substantially an output beam of polychromatic electromagnetic radiation having an even more relatively broadened and flattened intensity vs. wavelength over a wavelength spectrum comprising said comingled composite of a plurality of input beams of polychromatic electromagnetic radiation, (from sources (S1), (S2) and (S3)) projected along a common locus. It is emphasized that the sources (S1), (S2) and (S3) individually do not provide such an even more relatively broadened and flattened intensity vs. wavelength over a wavelength spectrum characteristic and thereby is demonstrated the utility of the present invention.

A system as shown in FIG. 2a1 preferably include a pivot(s) (PV) (PV') to allow the beam combining means (BCM) and/or (BCM'), respectively, to be rotated. A direct application of the use of pivot(s) (PV), particularly where two degrees of rotational freedom are allowed thereby, is to allow making beam combining means transmitted and reflected electromagnetic beam components coincident in output beams (OB) and (OB'). Where sources of electromagnetic beams (S2) and (S3) can be moved, pivot(s) (PV) can also be beneficially applied to allow selection of an optimum angle at which a beam of electromagnetic radiation is caused to reflect from a beam combining means in use. The reason this might be desirable is that the angle at which a beam of electromagnetic radiation approaches a beam combining means affects the percent of an impinging beam which actually reflects therefrom and becomes part of the output beam (OB). (Note, this is better discussed with respect to FIGS. 8a–8c supra).

FIG. 2a2 shows a single stage present invention system for providing an output beam (OB) of polychromatic electromagnetic radiation which has a relatively broad and flattened intensity vs. wavelength characteristic over a wavelength spectrum, as in FIG. 2a1. The Beam Combining Means (BCM) is rotated to change the angle at which the electromagnetic beam from source (S2) reflects therefrom. Where adjustment of the location(s) of source(s) (S1) and (S2) is possible, the pivot (PV) capability can be useful where one of the sources (S1) and/or (S2) of electromagnetic radiation provides an Intensity which too great or too little when, for instance, a forty-five degree tilt is applied to the beam combining means (BCM), as rotating said beam combining means (BCM) about said pivot (PV) allows adjustment of the Intensity of electromagnetic radiation wavelengths from the sources (S1) (S2), present in the Output Beam (OB). However, the pivot (PV) capability, (particularly where two degrees of rotational freedom are provided thereby such as where a globe and ball configuration is utilized), is primarily applied to allow beam combining means (BCM) transmitted (IB1) and reflected (IB2) beams to be oriented along a coincident locus in output beam (OB).

Figure 2C:
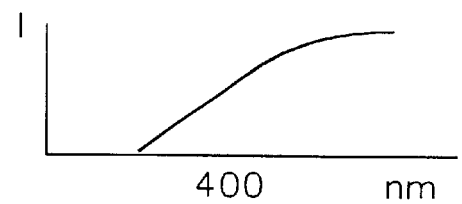
FIG. 2c demonstrates a beam of polychromatic electromagnetic radiation (IB2) from said second (S2) source of polychromatic electromagnetic radiation reflects from said at least one electro magnetic beam combining means (BCM).
Figure 2D:
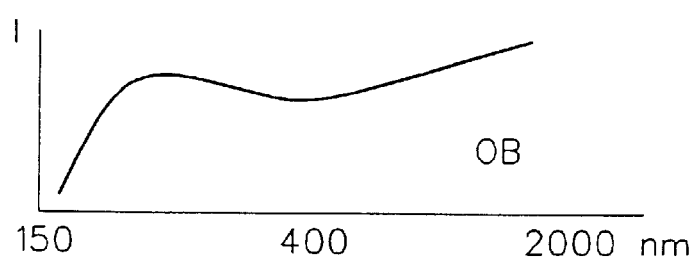
FIG. 2d demonstrates a resultant beam of polychromatic electromagnetic radiation (OB) which is substantially a comingled composite of a plurality of input beams (IB1) and (IB2) of polychromatic electromagnetic radiation which individually do not provide such a relatively broad and flattened intensity vs. wavelength over a wavelength spectrum characteristic as demonstrated in FIGS. 2b and 2c.

FIG. 2b demonstrates a spectrum of a polychromatic electromagnetic radiation (IB1) from said first source (S1) of polychromatic electromagnetic radiation which passes through said at least one electromagnetic beam combining means (BCM). FIG. 2c demonstrates a beam of polychromatic electromagnetic radiation (IB2) from said second (S2) source of polychromatic electromagnetic radiation reflects from said at least one electromagnetic beam combining means (BCM). FIG. 2d demonstrates a resultant beam of polychromatic electromagnetic radiation (OB) which is substantially a comingled composite of a plurality of input beams (IB1) and (IB2) of polychromatic electromagnetic radiation which individually do not provide such a relatively broad and flattened intensity vs. wavelength over a wavelength spectrum characteristic as demonstrated in FIGS. 2b and 2c.

Figure 8A:
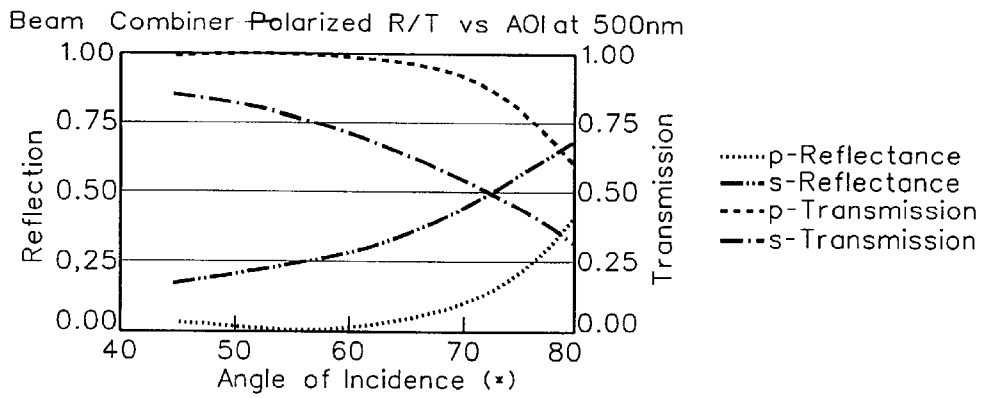
FIGS. 8a, 8b and 8c show various results for "P" and "S" polarized electromagnetic radiation components of various wavelengths which interacts with an uncoated thin fused silica plate beam combining means at various angles-of-incidence.
Figure 8B:
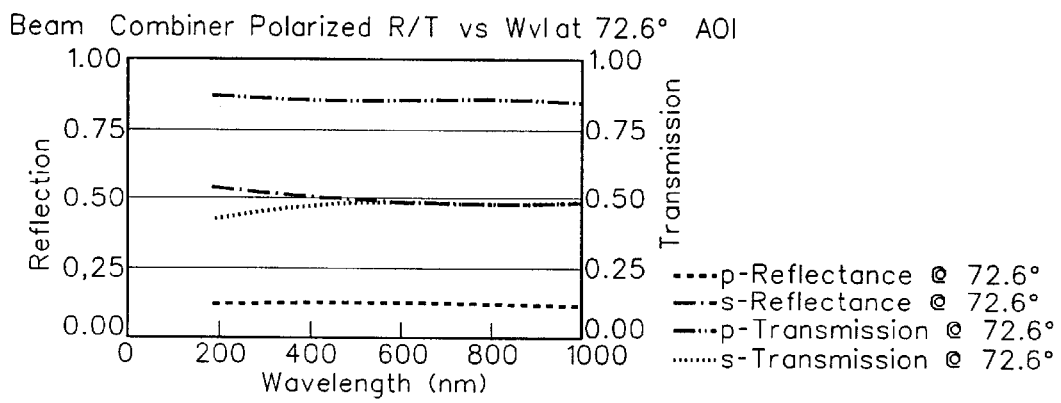
Figure 8C:
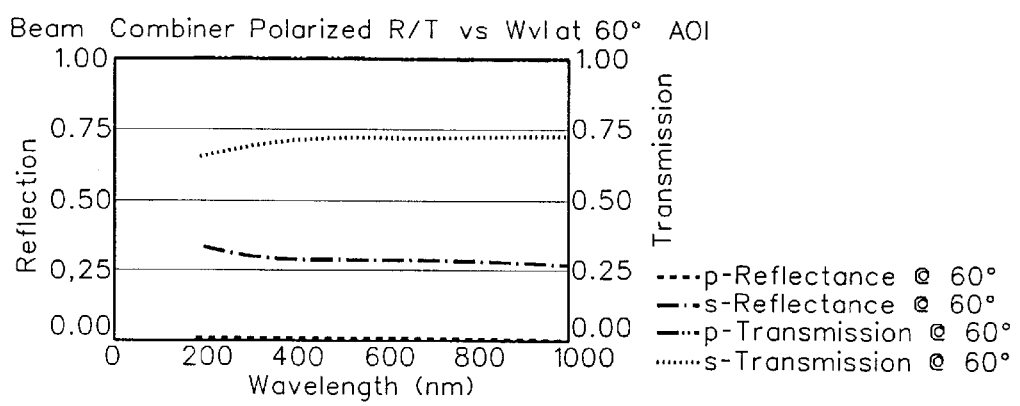

At this point, attention is directed to FIGS. 8a, 8b and 8c. As mentioned, electromagnetic beam intensity reflected and transmitted from an electromagnetic beam combining means (BCM) is a strong function of the polarization state and angle of incidence of said electromagnetic beam to said electromagnetic beam combining means (BCM), and electromagnetic beam combining means (BCM) tend to be most useful, (in terms of combining useful amounts of light from both Sources (S1) and (S2) when "S" Polarized electromagnetic radiation is present. Strong Brewster angle characteristics, (which cause nearly one-hundred (100%) percent transmission and zero (0.0%) percent reflection for "P" Polarized electromagnetic radiation over much of the angle-of-incidence range), limit the utility of the electromagnetic beam combining means (BCM) for "P" Polarized electromagnetic radiation. FIG. 8a shows Reflection and Transmission (R/T) results of a electromagnetic beam combining means (BCM) over a range of angles-of-incidence of between forty (40) and eighty (80) degrees. Note that at an angles-of-incidence of approximately seventy-three degrees "S" Transmission and Reflection are approximately equal. FIG. 8b shows the result where the angle-of-incidence is fixed at seventy-two-and-six-tenths (72.6) degrees, and wavelengths are scanned over the range of from one-hundred-ninety (190) and one-thousand (1000) nanometers, and FIG. 8c shows a similar plot where the angle-of-incidence is set to sixty (60) degrees. In all of the FIGS. 8a–8c note that the "P" Polarized electromagnetic radiation is less equally split between Transmission (T) and Reflection (R) than is the "IS" Polarization electromagnetic radiation, as near the Brewster angle, nearly all "P" Polarized electromagnetic radiation is transmitted. FIGS. 8a, 8b and 8c then provide insight as to why a Polarizer or Polarization State Generator (P), as shown in systems in FIGS. 1, 3, 4, 5 and 6, (discussed otherwise herein), should typically be adjusted and set to collect predominately "S" Polarized electromagnetic radiation from the beam combiner. It is pointed-out that use of the "S" component is particularly relevant in rotating compensator ellipsometer systems, wherein the polarizer remains fixed in position during data acquisition.

Figure 9A:
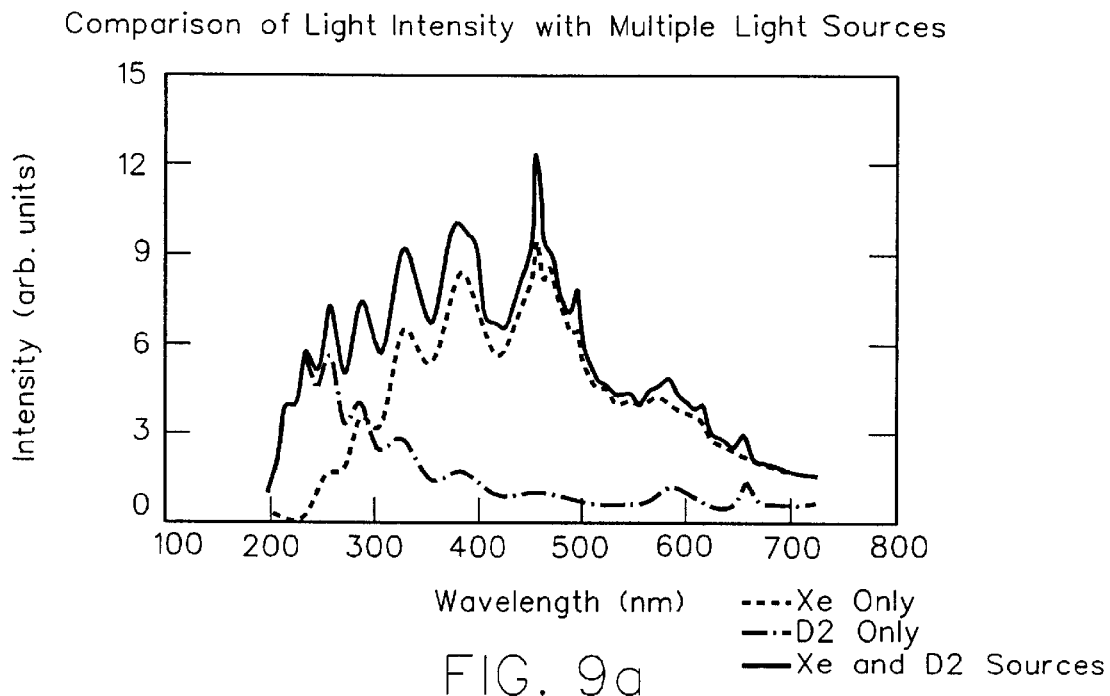
FIGS. 9a and 9b show actual results wherein Xenon and Deuterium Sources and here Dueterium and Quartz-Halogen Sources are combined, respectively.
Figure 9B:
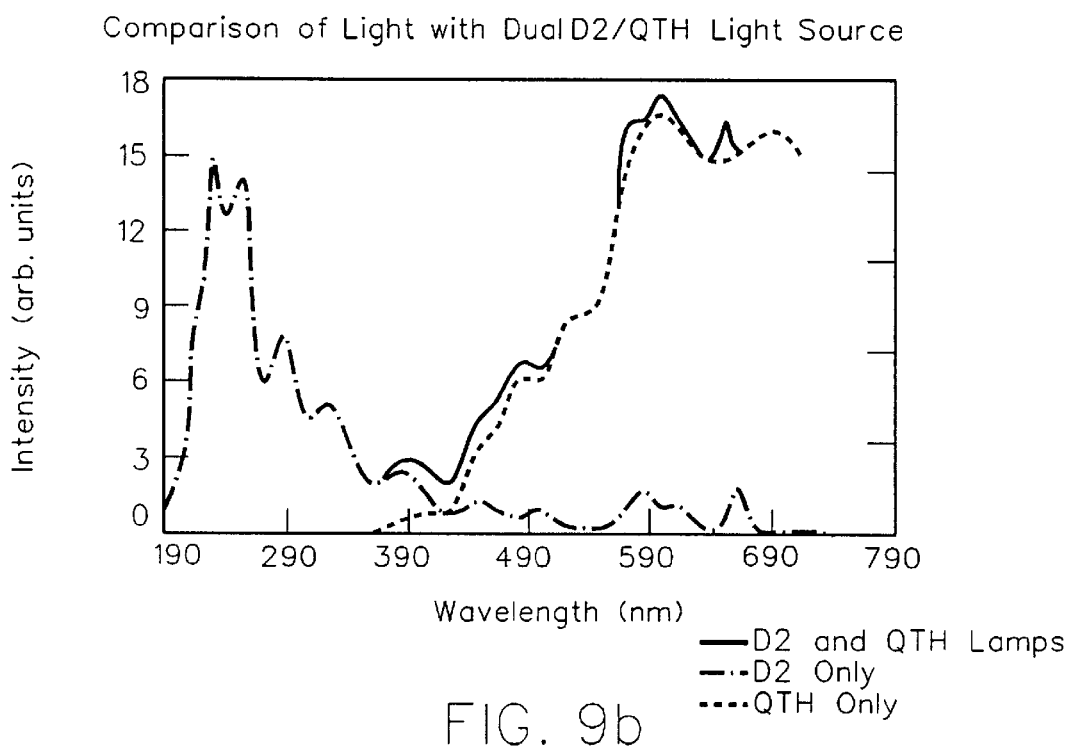

Before turning to a discussion of various specific system types into which the present invention can be utilized, attention is directed to FIGS. 9a and 9b which show actual output spectra results wherein Xenon and Deuterium Sources, and wherein Dueterium and Quartz-Halogen Sources are combined, respectively. Note that the Dueterium Source provides wavelengths at the low end wavelength ranges in both FIGS. 9a and 9b, via a present invention electromagnetic beam combining means (BCM). Both FIGS. 9a and 9b comprise electromagnetic beam combining means (BCM) rotated so that a reflected beam of electromagnetic radiation is caused to approach the surface thereof from a source (S2) in FIGS. 2a1 and 2a2, at an angle-of-incidence of sixty (60) degrees to a normal to said surface, thereby resulting in an approximately three to one (3/1) Transmission to Reflection Ratio. The results in FIG. 9a were achieved with electromagnetic radiation from a Xenon Lamp Source (S1) entered to a Beam Combining Means (BCM) through a small aperture, thus much of the originally available Xenon Intensity was lost prior to its transmission through the electromagnetic Beam Combining Means (BCM). FIG. 9b shows the results where a reflected electromagnetic beam from a Quartz Halogen Lamp Source (S2) has a much lower original Intensity than does the Deuturium Lamp Source (S1) which provides a beam of electromagnetic radiation which is caused to pass through a Beam Combining Means (BCM). Use of the sixty (60) degree angle-of-incidence, which emphasizes the Transmitted electromagnetic beam by a factor of three (3) over the Reflected electromagnetic beam, is thus utilized beneficially.

Figure 3:
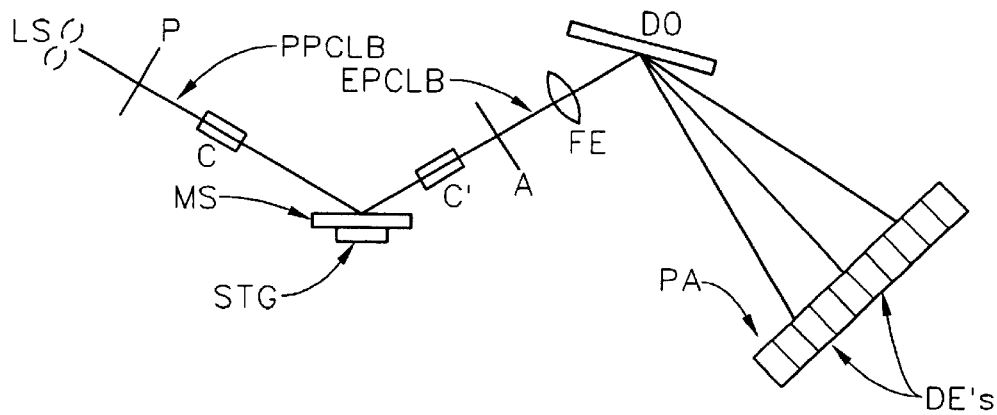
FIG. 3 shows a Spectroscopic Reflectance Mode version of the Rotating Compensator Material System Investigation System shown in FIG. 1, Detector Elements (DE's) containing Photo Array Detector System (DET) shown present directly after the Analyzer (A) and Dispersive Optics (DO).

Continuing, it is to be understood that the preferred system of the present invention Spectroscopic Rotating Compensator Material System Investigation System is basically found in a combination of components shown in FIGS. 1 and 2a1 & 2a2, the basic result of said combination, for a Reflectance Mode System, being shown in FIG. 3. That is, FIG. 3 shows a Spectroscopic Reflectance Mode version of the Rotating Compensator Material System Investigation System shown in FIG. 1, with the FIG. 3 Detector Elements (DE's) containing Photo Array Detector System (DET) shown present directly after the Analyzer (A).

Figure 4:
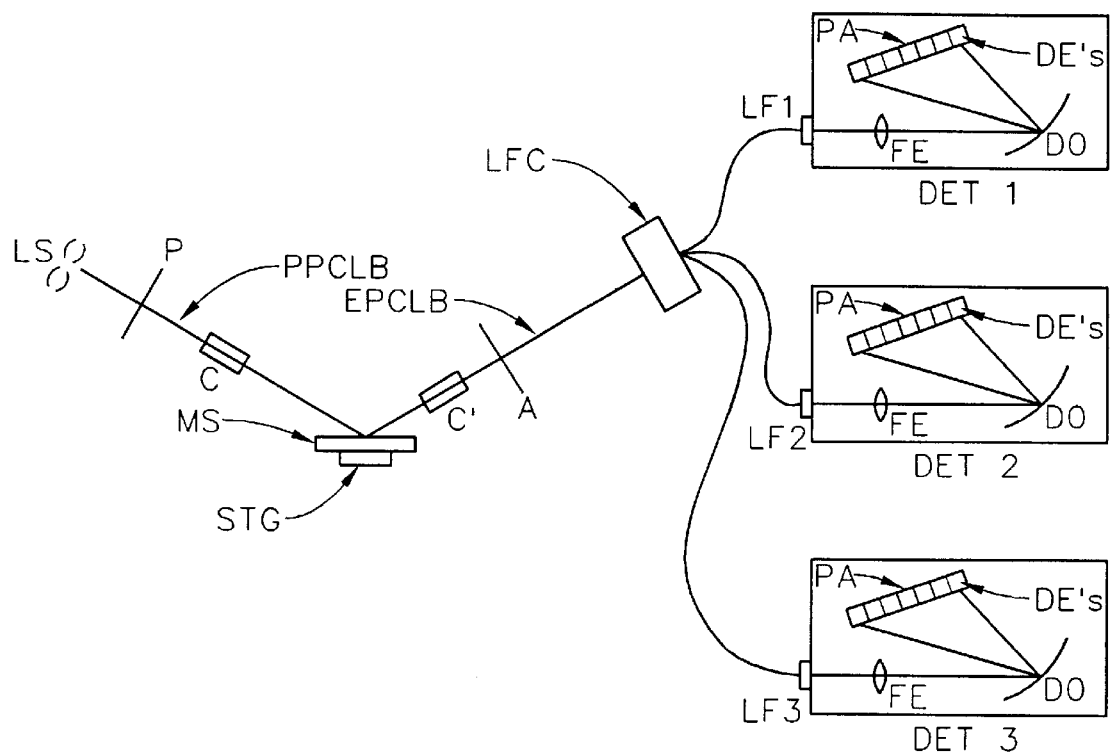
FIG. 4 shows a ther present invention system Reflectance Mode System configuration in which three (3) Detectors (Det 1), (Det 2) and (Det 3) are fed input by Fiber Optics (LF1), (LF2) and (LF3) present in a Fiber Optic Bundle exiting Fiber Optic Connector (LFC).

FIG. 4 shows another present invention system Reflectance Mode System configuration in which three (3) Detectors (Det 1), (Det 2) and (Det 3) are fed input by Fiber Optics (LF1), (LF2) and (LF3) present in a Fiber Optic Bundle exiting Fiber Optic Connector (LFC). Said Fiber Optic Connector (LFC) receives a Polarized Electromagnetic Beam (EPCLB) exiting the Analyzer (A).

Figure 5:
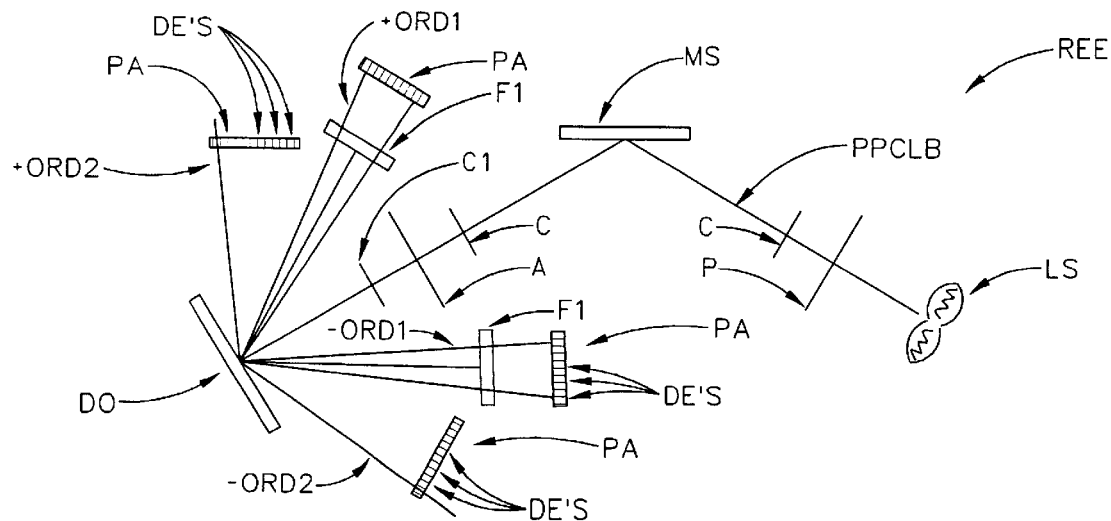
FIG. 5 show that the Reflected Polarized Beam of Electromagnetic Radiation (EPCLB), is caused to impinge upon a Dispersive Optics (DO), (eg. a Diffraction Grating), such that a plurality of Orders (+ORD2, +ORD1, −ORD1 and −ORD2) are produced.

FIG. 5 shows that the present invention can cause a Polychromatic Beam of Polarized Electromagnetic Radiation (PPCLB) to, after interaction with a Material System (MS), reflect therefrom. FIG. 5 shows that the Reflected Polarized Beam of Electromagnetic Radiation (EPCLB), is caused to impinge upon a Dispersive Optics (DO), (eg. a Diffraction Grating), such that a plurality of Orders (+ORD2, +ORD1, −ORD1 and −ORD2) are produced. Each said Order is comprised of a spectrum of Wavelengths, and FIG. 5 shows that Wavelengths in said Orders (+ORD2, +ORD1, −ORD1 and −ORD2) can be intercepted by Detector elements (DE's) in Photo Arrays (PA). The present invention can, in some embodiments, utilize such a system. It is noted that the Dispersive Optics (DO) is typically rotatable so that the direction each Order of wavelengths generally proceeds from said Dispersive Optics (DO) is adjustable. Note that FIG. 5 also shows the presence of Filters (F1). It is noted that Wavelengths for adjacent Orders overlap, and said Filters (F1) allow a user to pass only desired Wavelengths, as well as reduce background radiation entry to Photo Arrays (PA's). Typically a Focusing Element is not present in a FIG. 5 embodiment.

Figure 6:
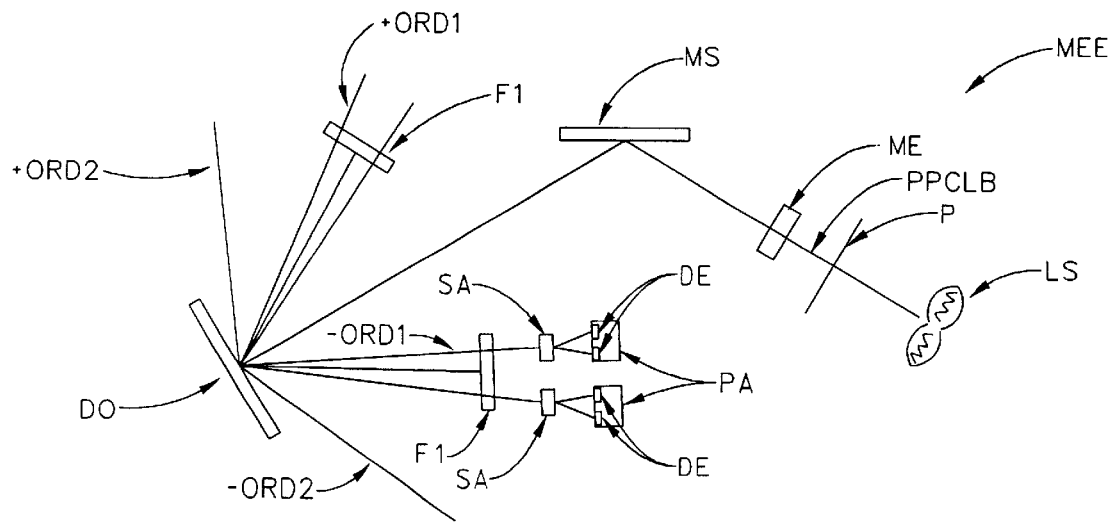
FIG. 6 is included to demonstrate that the present invention materials system investigation system can comprise a modulation element (MEE) ellipsometer system.

FIG. 6 is included to demonstrate that the present invention materials system investigation system can comprise a modulation element (MEE) ellipsometer system. Shown are a source of electromagnetic radiation (LS), a Polarizer (P), a Modulation Element (ME), a Material System (MS), a Dispersive Optics (DO), and Photo Array (PA) Detector Elements (DE) oriented to intercept a negative first order (−ORD1). Also shown is an order separating Filter (F) and beam Splitting Analyzers (SA).

It is noted that Fiber Optics can be utilized to carry Polychromatic Electromagnetic Radiation from a Source thereof (LS) to the position of a Polarizer (P), or from the position of an Analyzer (A) to a Detector (DET) in FIGS. 1, 3, 4, 5 and 6.

Analogically similar figures to those shown in FIGS. 3–6, but oriented for use in a Transmission Mode are not shown, but should be understood as within the scope of the present invention as implied by FIG. 1.

Figure 7:
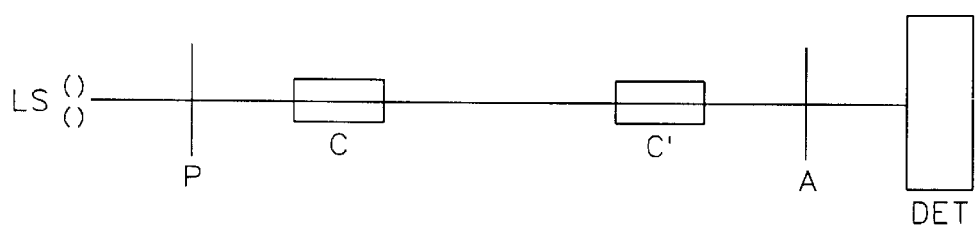
FIG. 7 demonstrates a present invention material system investigation system in a straight-through configuration.

FIG. 7 is included to identify that the present invention includes application in material system investigation systems in straight-through configurations. Such a configuration can be beneficial, for instance, during calibration procedures.

It is noted that any of said sources (S1) (S2) and (S3) of polychromatic electromagnetic radiation can be Xenon or Duterium, and Quartz-Halogen lamps, or other suitable source.

It is also noted that a suitable electromagnetic beam combining (BCM) means can be made of glass or a fused silica plate, (preferably uncoated), but can also be "Hot Mirrors" (which reflect IR and transmit visual wavelengths), or "Cold Mirrors" (which reflect visible and transmit IR); mirror-type Beam-splitters, or Pellicle Beam-splitters such as described in Edmund Industrial Optics Catalog Number N997A.

It is also generally noted that a preferred embodiment of the present invention Materials System Investigating System can utilize a Zeiss Diode Array Spectrometer System identified by manufacturer numbers in the group: (MMS1 (300–1150 nm); UV/VIS MMS (190–730 nm); UV MMS (190–400 nm); and IR MMS (900–2400 nm)) as Detector System (DET). Said identified Zeiss systems provide very compact systems comprising a multiplicity of Detector Elements (DE's), and provide focusing via a Focusing Element (FE), Slit, and single concave holographic grating dispersive optics (DO).

Having hereby disclosed the subject matter of this invention, it should be obvious that many modifications, substitutions and variations of the present invention are possible in light of the teachings. It is therefore to be understood that the present invention can be practiced other than as specifically described, and should be limited in breadth and scope only by the claims.

I claim:

1. A system for providing an output beam of polychromatic electromagnetic radiation which has a relatively broad and flattened intensity vs. wavelength characteristic over a wavelength spectrum, said output beam of polychromatic electromagnetic radiation substantially being a comingled composite of a plurality of input beams of polychromatic electromagnetic radiation which individually do not provide as relatively broad and flattened an intensity vs. wavelength characteristic over said wavelength spectrum, as does said output comingled composite beam of polychromatic electromagnetic radiation, said system for providing an output beam of polychromatic electromagnetic radiation which has a relatively broad and flattened intensity vs. wavelength characteristic over a wavelength spectrum comprising:

a. at least a first and a second source of polychromatic electromagnetic radiation; and b. at least a first electromagnetic beam combining means; said at least a first electromagnetic beam combining means being positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic;

said system for providing an output beam of polychromatic electromagnetic radiation which has a relatively broad and flattened intensity vs. wavelength characteristic over a wavelength spectrum being optionally further characterized by a selection from the group consisting of:

a1. a. a third source of electromagnetic radiation; and
b. a second electromagnetic beam combining means; said second electromagnetic beam combining means being positioned with respect to said comingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means, said second electromagnetic beam combining means being also positioned with respect to said third source of polychromatic electromagnetic radiation such that a beam of electromagnetic radiation from said third source of polychromatic electromagnetic radiation reflects from said second electromagnetic beam combining means such that a second resultant beam of polychromatic electromagnetic radiation which is substantially an output beam of polychromatic electromagnetic radiation which has a relatively even more broadened and flattened intensity vs. wavelength over a wavelength spectrum, comprising said comingled composite of a plurality of input beams of polychromatic electromagnetic radiation from said first, second and third sources, which first, second and third sources individually do not provide such a relatively even more broadened and flattened intensity vs. wavelength over a wavelength spectrum characteristic; and
a2. at least one of said first and second electromagnetic beam combining means is pivotally mounted in said system for providing an output beam of polychromatic electromagnetic radiation which has a relatively broad and flattened intensity vs. wavelength characteristic over a wavelength spectrum to allow rotation thereof, such that the angle at which a beam of polychromatic electromagnetic radiation from said second or third source of polychromatic electromagnetic radiation reflects from said first or second, respectively, electromagnetic beam combining means can be controlled.

2. A material system investigation system comprising:
a. a source of polychromatic electromagnetic radiation;
b. a polarization state setting system;
c. a means for supporting a material system;
d. a polarization state detection system; such that in use a beam of polychromatic electromagnetic radiation is caused to be provided by said source of polychromatic electromagnetic radiation, pass through said polarization state setting system, interact with a material system on said means for supporting a material system, and enter said polarization state detection system;
said source of polychromatic electromagnetic radiation comprising:
a system for providing an output beam of polychromatic electromagnetic radiation which has a relatively broad and flattened intensity vs. wavelength characteristic over a wavelength spectrum, said output beam of polychromatic electromagnetic radiation substantially being a comingled composite of a plurality of input beams of polychromatic electromagnetic radiation which individually do not provide as relatively broad and flattened an intensity vs. wavelength characteristic over said wavelength spectrum, as does said output beam of polychromatic electromagnetic radiation, said system for providing an output beam of polychromatic electromagnetic radiation which has a relatively broad and flattened intensity vs. wavelength characteristic over a wavelength spectrum comprising:
a. at least a first and a second source of polychromatic electromagnetic radiation; and
b. at least one electromagnetic beam combining means; said at least one electromagnetic beam combining means being positioned with respect to said first and second sources of polychromatic electromagnetic radiation such that a beam of polychromatic electromagnetic radiation from said first source of polychromatic electromagnetic radiation passes through said at least one electromagnetic beam combining means, and such that a beam of polychromatic electromagnetic radiation from said second source of polychromatic electromagnetic radiation reflects from said at least one electromagnetic beam combining means and is comingled with said beam of polychromatic electromagnetic radiation from said first source of polychromatic electromagnetic radiation which passes through said at least one electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

3. A material system investigation system as in claim 2, which is a selection from the group consisting of:
a. an ellipsometer system;
b. a spectrophotometer system; and
c. a polarimeter system.

4. A material system investigation system as in claim 2, in which said polarization state setting system is comprised of a polarizer optionally combined with a compensator.

5. A material system investigation system as in claim 2, in which said polarization state detection system is comprised of an analyzer and a multi-element containing detector system for simultaneously intercepting a plurality of wavelengths.

6. A spectroscopic rotating compensator material system investigation system comprising a source of a polychromatic beam of polychromatic electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator (s) positioned at a location selected from the group consisting of:
before said stage for supporting a material system;
after said stage for supporting a material system; and
both before and after said stage for supporting a material system; such that when said spectroscopic rotating compensator material system investigation system is used to investigate a material system present on said stage for supporting a material system, said analyzer and polarizer are maintained essentially fixed in position and at least one of said at least one compensator(s)

is caused to continuously rotate while a beam of polychromatic polychromatic electromagnetic radiation produced by said source of a beam of polychromatic polychromatic electromagnetic radiation is caused to pass through said polarizer and said compensator(s), said beam of polychromatic polychromatic electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

wherein said source of a beam of polychromatic polychromatic electromagnetic radiation comprises:
   a system for providing an output beam of polychromatic electromagnetic radiation which has a relatively broad and flattened intensity vs. wavelength characteristic over a wavelength spectrum, said output beam of polychromatic electromagnetic radiation being a comingled composite of a plurality of input beams of polychromatic electromagnetic radiation which individually do not provide as relatively broad and flattened an intensity vs. wavelength characteristic over said wavelength spectrum, as does said output beam of polychromatic electromagnetic radiation, said system for providing an output beam of polychromatic electromagnetic radiation which has a relatively broad and flattened intensity vs. wavelength characteristic over a wavelength spectrum comprising:
     a. at least a first and a second source of polychromatic electromagnetic radiation; and
     b. at least one electromagnetic beam combining means; said at least one electromagnetic beam combining means being positioned with respect to said first and second sources of polychromatic electromagnetic radiation such that a beam of polychromatic electromagnetic radiation from said first source of polychromatic electromagnetic radiation passes through said at least one electromagnetic beam combining means, and such that a beam of polychromatic electromagnetic radiation from said second source of polychromatic electromagnetic radiation reflects from said at least one electromagnetic beam combining means and is comingled with said beam of polychromatic electromagnetic radiation from said first source of polychromatic electromagnetic radiation which passes through said at least one electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

7. A spectroscopic rotating compensator material system investigation system as in claim 6 in which the compensator(s) is/are non-achromatic in that retardation effected thereby between orthogonal components of a beam of polychromatic electromagnetic radiation at one wavelength is different than that provided thereby at at least one other wavelength.

8. A spectroscopic rotating compensator material system investigation system comprising a source of a polychromatic beam of polychromatic electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator positioned at a location selected from the group consisting of:
   before said stage for supporting a material system;
   after said stage for supporting a material system; and
   before and after said stage for supporting a material system; such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a beam of polychromatic polychromatic electromagnetic radiation produced by said source of a beam of polychromatic polychromatic electromagnetic radiation is caused to pass through said polarizer and said compensator(s), said beam of polychromatic polychromatic electromagnetic radiation being also caused to interact with said material system; said beam of polychromatic polychromatic electromagnetic radiation being also, without further focusing, caused to pass through said analyzer and interact with said dispersive optics, said dispersive optics serving to form a plurality of essentially spatially offset orders (+ORD2) (+ORD1) (−ORD1) (−ORD2) when said beam of polychromatic polychromatic electromagnetic radiation is caused to impinge thereupon, each said produced order (+ORD2) (+ORD1) (−ORD1) (−ORD2) comprising an essentially continuous spectrum of spatially separated polychromatic electromagnetic beams of essentially single wavelengths, many of said essentially single wavelengths being present in two or more produced orders (+ORD2) (+ORD1) (−ORD1) (−ORD2); such that in use first and second multiplicities of essentially single wavelength beams of polychromatic electromagnetic radiation from first and second produced orders can be simultaneously intercepted by, respectively, first and second detector systems, thereby enabling the simultaneous accessing of a first multiplicity of essentially single wavelengths by said first detector system and a second multiplicity of essentially single wavelengths by said second detector system, each of which first and second multiplicities of essentially single wavelengths includes specific first and second essentially single wavelength beams of polychromatic electromagnetic radiation, said specific first and second essentially single wavelength beams of polychromatic electromagnetic radiation being possible to simultaneously intercept by specific detector elements in said first and second detector systems respectively, even where polychromatic electromagnetic beams of said specific first and second essentially single wavelengths are spatially situated to close to one another in a single produced order for separate photo detector array detector elements in a single detector system which intercepts said single order, to, simultaneously, access beams of polychromatic electromagnetic radiation of both said specific first and second essentially single wavelengths, separately;

said source of a beam of polychromatic polychromatic electromagnetic radiation comprising:
a system for providing an output beam of polychromatic electromagnetic radiation which has a relatively broad and flattened intensity vs. wavelength characteristic over a wavelength spectrum, said output beam of polychromatic electromagnetic radiation being a comingled composite of a plurality of input beams of polychromatic electromagnetic radiation which individually do not provide as relatively broad and flattened an intensity vs. wavelength characteristic over said wavelength spectrum, as does said output beam of polychromatic electromagnetic radiation, said system for providing an output beam of polychromatic electromagnetic radiation which has a relatively broad and flattened intensity vs. wavelength characteristic over a wavelength spectrum comprising:
  a. at least a first and a second source of polychromatic electromagnetic radiation; and
  b. at least one electromagnetic beam combining means; said at least one electromagnetic beam combining means being positioned with respect to said first and second sources of polychromatic electromagnetic radiation such that a beam of polychromatic electromagnetic radiation from said first source of polychromatic electromagnetic radiation passes through said at least one electromagnetic beam combining means, and such that a beam of polychromatic electromagnetic radiation from said second source of polychromatic electromagnetic radiation reflects from said at least one electromagnetic beam combining means and is comingled with said beam of polychromatic electromagnetic radiation from said first source of polychromatic electromagnetic radiation which passes through said at least one electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

9. A spectroscopic material system investigation system comprising a source of a beam of polychromatic polychromatic electromagnetic radiation, a polarizer, a stage for supporting a material system, an analyzer, a dispersive optics and at least one detector system which contains a multiplicity of detector elements, said spectroscopic material system investigation system optionally comprising one or more compensators positioned at a location selected from the group consisting of:
  before said stage for supporting a material system;
  after said stage for supporting a material system; and
  before and after said stage for supporting a material system; such that when said spectroscopic material system investigation system is used to investigate a material system present on said stage for supporting a material system, a selection from the group consisting of:

said polarizer; and
said analyzer; is caused to continuously rotate while a beam of polychromatic polychromatic electromagnetic radiation produced by said source of a beam of polychromatic polychromatic electromagnetic radiation is caused to pass through said polarizer and any present compensators, said polychromatic beam of polychromatic electromagnetic radiation being also caused to interact with said material system; said beam of polychromatic polychromatic electromagnetic radiation being also, without further focusing, caused to pass through said analyzer and interact with said dispersive optics, said dispersive optics serving to form a plurality of essentially spatially offset orders (+ORD2) (+ORD1) (−ORD1) (−ORD2) when said beam of polychromatic polychromatic electromagnetic radiation is caused to impinge thereupon, each said produced order (+ORD2) (+ORD1) (−ORD1) (−ORD2) comprising an essentially continuous spectrum of spatially separated polychromatic electromagnetic beams of essentially single wavelengths, many of said essentially single wavelengths being present in two or more produced orders (+ORD2) (+ORD1) (−ORD1) (−ORD2); such that in use first and second multiplicities of essentially single wavelength beams of polychromatic electromagnetic radiation from first and second produced orders can be simultaneously intercepted by, respectively, first and second detector systems, thereby enabling the simultaneous accessing of a first multiplicity of essentially single wavelengths by said first detector system and a second multiplicity of essentially single wavelengths by said second detector system, each of which first and second multiplicities of essentially single wavelengths includes specific first and second essentially single wavelength beams of polychromatic electromagnetic radiation, said specific first and second essentially single wavelength beams of polychromatic electromagnetic radiation being possible to simultaneously intercept by specific detector elements in said first and second detector systems respectively, even where polychromatic electromagnetic beams of said specific first and second essentially single wavelengths are spatially situated to close to one another in a single produced order for separate photo detector array detector elements in a single detector system which intercepts said single order, to, simultaneously, access beams of polychromatic electromagnetic radiation of both said specific first and second essentially single wavelengths, separately;

said source of a beam of polychromatic polychromatic electromagnetic radiation comprising:
a system for providing an output beam of polychromatic electromagnetic radiation which has a relatively broad and flattened intensity vs. wavelength characteristic over a wavelength spectrum, said output beam of polychromatic electromagnetic radiation being a comingled composite of a plurality of input beams of polychromatic electromagnetic radiation which individually do not provide as relatively broad and flattened an intensity vs. wavelength characteristic over said wavelength spectrum, as does said output beam of polychromatic electromagnetic radiation, said system for providing an output beam of polychromatic electromagnetic radiation which has a relatively broad and flattened intensity vs. wavelength characteristic over a wavelength spectrum comprising:
- a. at least a first and a second source of polychromatic electromagnetic radiation; and
- b. at least one electromagnetic beam combining means; said at least one electromagnetic beam combining means being positioned with respect to said first and second sources of polychromatic electromagnetic radiation such that a beam of polychromatic electromagnetic radiation from said first source of polychromatic electromagnetic radiation passes through said at least one electromagnetic beam combining means, and such that a beam of polychromatic electromagnetic radiation from said second source of polychromatic electromagnetic radiation reflects from said at least one electromagnetic beam combining means and is comingled with said beam of polychromatic electromagnetic radiation from said first source of polychromatic electromagnetic radiation which passes through said at least one electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

10. A spectroscopic material system investigation system, adapted to sense characteristics of a material system comprising;

a source of polychromatic electromagnetic radiation;

a polarization state generator;

an analyzer; and a diffraction grating and a colliminator; positioned so that electromagnetic radiation passing through the analyzer without further focusing after interacting with the material system transmits into said detector; wherein the diffraction grating reflects electromagnetic radiation into the detector at a predetermined angle with respect to a normal to the diffraction grating with a precision of at least plus or minus one-half degree;

said source of polychromatic electromagnetic radiation comprising:
a system for providing an output beam of polychromatic electromagnetic radiation which has a relatively broad and flattened intensity vs. wavelength characteristic over a wavelength spectrum, said output beam of polychromatic electromagnetic radiation being a comingled composite of a plurality of input beams of polychromatic electromagnetic radiation which individually do not provide as relatively broad and flattened an intensity vs. wavelength characteristic over said wavelength spectrum, as does said output beam of polychromatic electromagnetic radiation, said system for providing an output beam of polychromatic electromagnetic radiation which has a relatively broad and flattened intensity vs. wavelength characteristic over a wavelength spectrum comprising:
- a. at least a first and a second source of polychromatic electromagnetic radiation; and
- b. at least one electromagnetic beam combining means; said at least one electromagnetic beam combining means being positioned with respect to said first and second sources of polychromatic electromagnetic radiation such that a beam of polychromatic electromagnetic radiation from said first source of polychromatic electromagnetic radiation passes through said at least one electromagnetic beam combining means, and such that a beam of polychromatic electromagnetic radiation from said second source of polychromatic electromagnetic radiation reflects from said at least one electromagnetic beam combining means and is comingled with said beam of polychromatic electromagnetic radiation from said first source of polychromatic electromagnetic radiation which passes through said at least one electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

11. A spectroscopic material system investigation system, adapted to sense characteristics of a material system comprising;
- a. a source of polychromatic electromagnetic radiation;
- b. a polarizer;
- c. a stage for supporting a material system;
- d. an analyzer;
- e. a dispersive optics;
- f. at least one detector system which contains a multiplicity of detector elements; and
- g. a modulation element positioned at at least one location selected from the group consisting of:
  before said stage for supporting a material system;
  after said stage for supporting a material system; and
  before and after said stage for supporting a material system; such that when said spectroscopic material system investigation system is used to investigate a material system present on said stage for supporting a material system, said modulation element is caused to modulate a beam of polychromatic electromagnetic radiation produced by said source of a beam of polychromatic electromagnetic radiation is caused to pass through said polarizer, said polychromatic beam of electromagnetic radiation being also caused to interact with said material system and pass through said analyzer and enter said detector system;

said source of polychromatic electromagnetic radiation comprising:
a system for providing an output beam of polychromatic electromagnetic radiation which has a relatively broad and flattened intensity vs. wavelength characteristic over a wavelength spectrum, said output beam of polychromatic electromagnetic radiation being a comingled composite of a plurality of input beams of polychromatic electromagnetic radiation which individually do not provide as relatively broad and flattened intensity vs. wavelength characteristic over said wavelength spectrum, as does said output beam of polychromatic electromagnetic radiation, said system for providing an output beam of polychromatic electromagnetic radiation which has a relatively broad and flattened intensity vs. wavelength characteristic over a wavelength spectrum comprising:
  a. at least a first and a second source of polychromatic electromagnetic radiation; and
  b. at least one electromagnetic beam combining means; said at least one electromagnetic beam combining means being positioned with respect to said first and second sources of polychromatic electromagnetic radiation such that a beam of polychromatic electromagnetic radiation from said first source of polychromatic electromagnetic radiation passes through said at least one electromagnetic beam combining means, and such that a beam of polychromatic electromagnetic radiation from said second source of polychromatic electromagnetic radiation reflects from said at least one electromagnetic beam combining means and is comingled with said beam of polychromatic electromagnetic radiation from said first source of polychromatic electromagnetic radiation which passes through said at least one electromagnetic beam combining means, said resultant beam of polychromatic electromagnetic radiation substantially being said output beam of polychromatic electromagnetic radiation which has a relatively broad and flattened intensity vs. wavelength over a wavelength spectrum, comprising said comingled comingled composite of a plurality of input beams of polychromatic electromagnetic radiation which individually do not provide such a relatively broad and flattened intensity vs. wavelength over a wavelength spectrum characteristic.

12. A material system investigation system as in claim 2, characterized by at least one selection from the group consisting of:
  said a polarization state setting system is aligned so as to pass predominately "S" polarized electromagnetic radiation, as referred to the beam combiner, from said source of polychromatic electromagnetic radiation; and
  said at least one electromagnetic beam combining means optionally is pivotally mounted in said material system investigation system to allow rotation thereof, such that the angle at which a beam of polychromatic electromagnetic radiation from said second source of polychromatic electromagnetic radiation reflects from said at least one electromagnetic beam combining means can be controlled to place it coincident with a transmitted beam of electromagnetic radiation therethrough; and
  said beam combining means is an uncoated transparent plate.

13. A material system investigation system as in claim 3, characterized by at least one selection from the group consisting of:
  said a polarization state setting system is aligned so as to pass predominately "S" polarized electromagnetic radiation, as referred to the beam combining means, from said source of polychromatic electromagnetic radiation; and
  said at least one electromagnetic beam combining means optionally is pivotally mounted in said material system investigation system to allow rotation thereof, such that the angle at which a beam of polychromatic electromagnetic radiation from said second source of polychromatic electromagnetic radiation reflects from said at least one electromagnetic beam combining means can be controlled to place it coincident with a transmitted beam of electromagnetic radiation therethrough; and
  said beam combining means is an uncoated transparent plate.

14. A spectroscopic rotating compensator material system investigation system as in claim 6, characterized by at least one selection from the group consisting of:
  said polarizer is aligned so as to pass predominately "S" polarized electromagnetic radiation, as referred to the beam combining means, from said source of polychromatic electromagnetic radiation; and
  said at least one electromagnetic beam combining means optionally is pivotally mounted in said spectroscopic rotating compensator material system investigation system to allow rotation thereof, such that the angle at which a beam of polychromatic electromagnetic radiation from said second source of polychromatic electromagnetic radiation reflects from said at least one electromagnetic beam combining means can be controlled to place it coincident with a transmitted beam of electromagnetic radiation therethrough; and
  said beam combining means is an uncoated transparent plate.

15. A spectroscopic rotating compensator material system investigation system as in claim 8, characterized by at least one selection from the group consisting of:
  said polarizer is aligned so as to pass predominately "S" polarized electromagnetic radiation, as referred to the beam combining means, from said source of polychromatic electromagnetic radiation; and
  said at least one electromagnetic beam combining means optionally is pivotally mounted in said spectroscopic rotating compensator material system investigation system to allow rotation thereof, such that the angle at which a beam of polychromatic electromagnetic radiation from said second source of polychromatic electromagnetic radiation reflects from said at least one electromagnetic beam combining means can be controlled to place it coincident with a transmitted beam of electromagnetic radiation therethrough; and
  said beam combining means is an uncoated transparent plate.

16. A spectroscopic material system investigation system as in claim 9, characterized by at least one selection from the group consisting of:
  said polarizer is aligned so as to pass predominately "S" polarized electromagnetic radiation, as referred to the beam combining means, from said source of polychromatic electromagnetic radiation; and
  said at least one electromagnetic beam combining means optionally is pivotally mounted in said spectroscopic material system investigation system to allow rotation thereof, such that the angle at which a beam of polychromatic electromagnetic radiation from said second source of polychromatic electromagnetic radiation reflects from said at least one electromagnetic beam combining means can be controlled to place it coincident with a transmitted beam of electromagnetic radiation therethrough; and said beam combining means is an uncoated transparent plate.

17. A spectroscopic material system investigation system as in claim 10, characterized by at least one selection from the group consisting of:

said polarization state generator is aligned to pass predominately "S" polarized electromagnetic radiation, as referred to the beam combining means, from said source of polychromatic electromagnetic radiation; and said at least one electromagnetic beam combining means optionally is pivotally mounted in said spectroscopic material system investigation system to allow rotation thereof, such that the angle at which a beam of polychromatic electromagnetic radiation from said second source of polychromatic electromagnetic radiation reflects from said at least one electromagnetic beam combining means can be controlled to place it coincident with a transmitted beam of electromagnetic radiation therethrough; and said beam combining means is an uncoated transparent plate.

18. A spectroscopic material system investigation system as in claim 11, characterized by at least one selection from the group consisting of:

said polarizer is aligned to pass predominately "S" polarized electromagnetic radiation, as referred to the beam combining means, from said source of polychromatic electromagnetic radiation; and said at least one electromagnetic beam combining means optionally is pivotally mounted in said spectroscopic material system investigation system to allow rotation thereof, such that the angle at which a beam of polychromatic electromagnetic radiation from said second source of polychromatic electromagnetic radiation reflects from said at least one electromagnetic beam combining means can be controlled to place it coincident with a transmitted beam of electromagnetic radiation therethrough; and said beam combining means is an uncoated transparent plate.

* * * * *